United States Patent
Cade et al.

(10) Patent No.: US 9,655,860 B2
(45) Date of Patent: May 23, 2017

(54) HYDROXYPROPYL METHYL CELLULOSE HARD CAPSULES AND PROCESS OF MANUFACTURE

(71) Applicant: Capsugel Belgium NV, Bornem (BE)

(72) Inventors: Dominique Nicolas Cade, Colmar (FR); David He Xiongwei, Andolsheim (FR)

(73) Assignee: Capsugel Belgium NV, Bornem (BE)

( * ) Notice: Subject to any disclaimer, the term of this patent is extended or adjusted under 35 U.S.C. 154(b) by 0 days.

(21) Appl. No.: 15/378,856

(22) Filed: Dec. 14, 2016

(65) Prior Publication Data

US 2017/0087092 A1 Mar. 30, 2017

Related U.S. Application Data

(60) Division of application No. 14/860,316, filed on Sep. 21, 2015, which is a continuation of application No. 14/094,699, filed on Dec. 2, 2013, now abandoned, which is a division of application No. 12/446,624, filed as application No. PCT/IB2007/003160 on Oct. 17, 2007, now abandoned.

(60) Provisional application No. 60/863,190, filed on Oct. 27, 2006.

(51) Int. Cl.
*A61K 9/48* (2006.01)
*A61J 3/07* (2006.01)

(52) U.S. Cl.
CPC ............. *A61K 9/4833* (2013.01); *A61J 3/077* (2013.01); *A61K 9/4816* (2013.01)

(58) Field of Classification Search
USPC ........................................................ 424/451
See application file for complete search history.

(56) References Cited

U.S. PATENT DOCUMENTS

| | | | |
|---|---|---|---|
| 2,526,683 A | 10/1950 | Murphy | |
| 3,493,407 A | 2/1970 | Greminger et al. | |
| 3,617,588 A | 11/1971 | Langman | |
| 4,001,211 A | 1/1977 | Sarkar | |
| 4,365,060 A | 12/1982 | Onda et al. | |
| 4,893,721 A | 1/1990 | Bodenmann et al. | |
| 5,264,223 A | 11/1993 | Yamamoto et al. | |
| 5,431,917 A | 7/1995 | Yamamoto et al. | |
| 5,431,919 A | 7/1995 | Maruyama et al. | |
| 5,756,123 A | 5/1998 | Yamamoto et al. | |
| 6,228,416 B1 | 5/2001 | Reibert et al. | |
| 6,326,026 B1 | 12/2001 | Parekh et al. | |
| 6,649,180 B1 | 11/2003 | Matsuura et al. | |
| 7,094,425 B2 | 8/2006 | Scott et al. | |
| 2010/0168410 A1 | 7/2010 | Cade et al. | |

FOREIGN PATENT DOCUMENTS

| | | |
|---|---|---|
| AU | 2007310534 | 2/2008 |
| BR | PI0717123 | 1/2014 |
| CA | 2667167 | 2/2014 |
| CN | 101595133 | 11/2012 |
| EP | 0246693 | 11/1987 |
| EP | 0401832 | 12/1990 |
| EP | 0592130 | 4/1994 |
| EP | 0714656 | 6/1996 |
| EP | 1045000 | 10/2000 |
| EP | 2078042 | 7/2009 |
| GB | 1310697 | 3/1973 |
| JP | 51-76417 | 7/1976 |
| JP | 62-266060 | 11/1987 |
| JP | 3-9755 | 1/1991 |
| JP | 22552937 | 11/1996 |
| JP | 5372761 | 12/2013 |
| KR | 20120038021 | 4/2012 |
| KR | 101170283 | 7/2012 |
| MX | 2009004434 | 5/2009 |
| RU | 2420538 | 6/2011 |
| WO | WO98/27151 | 6/1998 |
| WO | WO01/95941 | 12/2001 |
| WO | WO02/064132 | 8/2002 |
| WO | WO03/072139 | 9/2003 |
| WO | WO2008/050209 | 5/2008 |
| WO | WO03/011257 | 2/2013 |

OTHER PUBLICATIONS

Sammon, Chris et al., "The application of attenuated total reflectance Fourier transform infrared spectroscopy to monitor the concentration and state of water in solutions of a thermally responsive cellulose ether during gelation," *Polymer*, 47(2):577-584 (Jan. 2006).

Basak, "HPMC: A versatile hydrophilic polymer," http://saffron.pharmabiz.com/article/detnews.asp?articleid=35878&sectionid=50 (Nov. 2, 2006).

Dow, http://msdssearch.dow.com/PublishedLiteratureDOWCOM/dh_0379/0901b803803797ad.pdf?filepath=methocel/pdfs/noreg/198-02075.pdf&fromPage=GetDoc (accessed Dec. 14, 2014).

Final Rejection in Japanese Patent Application No. 2009-533976 (mailed Feb. 12, 2013).

Japanese Office Action dated from Japanese Patent Application No. 2009-533976 (mailed Sep. 4, 2012).

International Search Report for PCT/IB2007/003160 (mailed Mar. 20, 2008).

International Preliminary Report on Patentablility for PCT/IB2007/003160 (mailed Apr. 28, 2009).

Office Action from Australian Patent Application No. 2007310534 (mailed Feb. 21, 2012).

Office Action from Canadian Patent Application No. 2,667,167 (mailed Jan. 25, 2012).

(Continued)

*Primary Examiner* — Devang Thakor

(74) *Attorney, Agent, or Firm* — Klarquist Sparkman, LLP

(57) ABSTRACT

A composition for manufacture of hard hydroxypropyl methyl cellulose capsules comprising a film forming material of hydroxypropyl methyl cellulose having a methoxy content of 27.0-30.0% (w/w), and a hydroxypropoxy content of 4.0-7.5% and as a 2% weight solution, a viscosity of 3.5-6.0 cPs at 20° C., dipping compositions, process for manufacture of hard hydroxypropyl methyl cellulose capsules according to a dip coating process and hard capsule shells.

12 Claims, 1 Drawing Sheet

(56) References Cited

OTHER PUBLICATIONS

Office Action from Canadian Patent Application No. 2,667,167 (mailed Dec. 11, 2012).
Office Action from Chinese Patent Application No. 200780040028.6 (mailed Apr. 1, 2011).
Office Action for European Patent Application No. 07825456.2 (mailed Jan. 18, 2016).
Office Action from Indonesian Patent Application No. W-00200901072 (mailed Jan. 27, 2010).
Office Action from Indian Patent Application No. 2322/DELNP/2009 (mailed May 28, 2013).
Office Action from Korean Patent Application No. 2009-7008506 (mailed Mar. 7, 2011).
Office Action from Korean Patent Application No. 2009-7008506 (mailed Nov. 30, 2011).
Office Action from Mexican Patent Application No. MX/A/2009/004434 (mailed Mar. 21, 2013).
Office Action from Russian Patent Application No. 2009115682/05 (mailed Jun. 23, 2010).
Office Action from Thailand Patent Application No. 07001005400 (mailed Jul. 16, 2010).
Partial English-language translation of JP3-9755 and JP62-26606.
Written Opinion for PCT/IB2007/003160 (mailed Apr. 27, 2009).

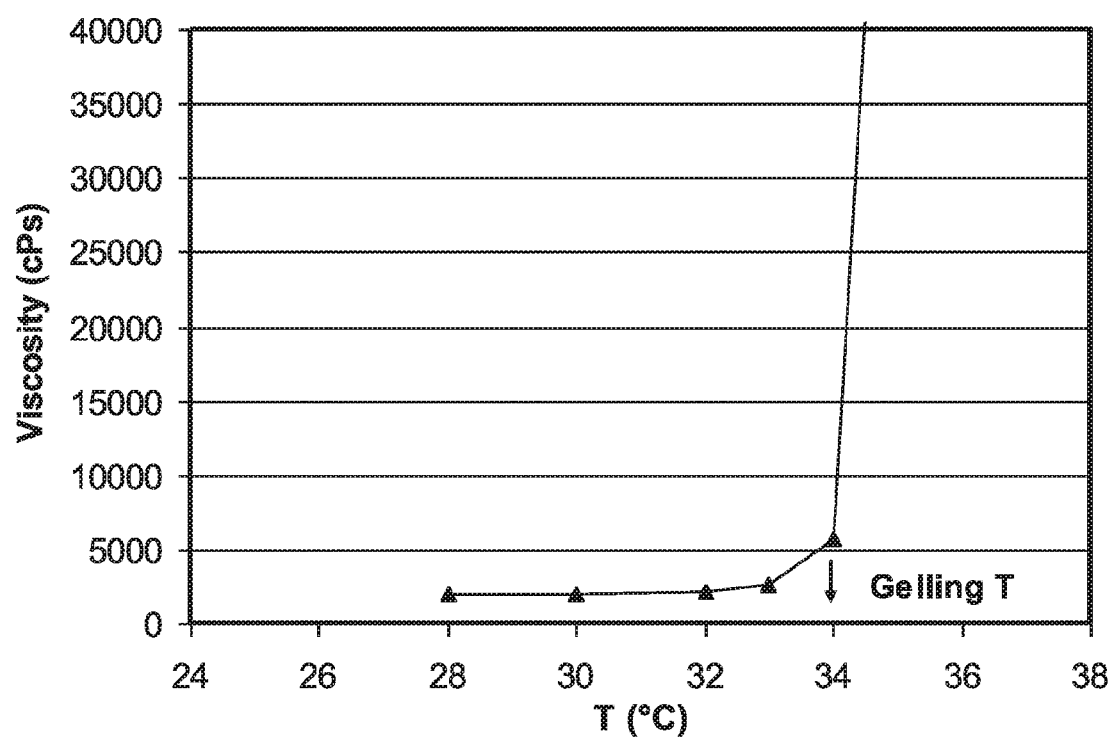

HYDROXYPROPYL METHYL CELLULOSE HARD CAPSULES AND PROCESS OF MANUFACTURE

CROSS REFERENCE TO RELATED APPLICATIONS

This application is a divisional of U.S. patent application Ser. No. 14/860,316, filed Sep. 21, 2015, which is a continuation of U.S. patent application Ser. No. 14/094,699, filed Dec. 2, 2013, now abandoned, which is a divisional of U.S. patent application Ser. No. 12/446,624, filed Feb. 25, 2010, now abandoned, which is a national stage entry under 35 U.S.C. §371 of International Application No. PCT/IB07/03160, filed Oct. 17, 2007 which claims the benefit of U.S. Provisional Application No. 60/863,190, filed Oct. 27, 2006, all of which are incorporated herein by reference.

The present invention relates to an aqueous composition for the manufacture of hydroxypropyl methyl cellulose (hereinafter also "HPMC") hard capsules, a method of preparing HPMC hard capsules and hard capsules obtained therewith.

Capsules are well-known dosage forms that normally consist of a shell filed with one or more specific substances. The shell may be a soft or, as in this invention, a hard stable shell comprising film-forming polymer(s) such as gelatine, modified starches, modified celluloses etc.

Hard capsules are generally manufactured by using a dip molding process. In this process, pin molds are dipped into a film forming composition. By gelling the film forming polymer on the pin, a film is formed that is subsequently dried on the pin, to obtain a capsule shells. The shells are then stripped of the pins and cut to a desired length. Thus, capsules caps and bodies are obtained that can later be filed with a substance and joined such that a filed capsule is obtained.

When using this type of dip molding process, it is necessary to ensure that the dipping composition adheres to the pin surface and quickly gels, once the pins are withdrawn from the dipping bath. This avoids that the composition flows on the pins surface so as to achieve the desired shell or film distribution to manufacture capsules.

When using gelatine as the film forming polymer, the dipping compositions gel with cooling. The same gelling behaviour is shown by mixtures of methyl celluloses and gelling agents. Both these types of film forming polymers may be processed on conventional devices for manufacturing hard gelatine capsules.

U.S. Pat. No. 2,526,683 discloses a process for preparing methyl cellulose medicinal capsules by a dip coating process. The process consists of dipping a capsule forming pin pre-heated to 40° C.-85° C. into a methyl cellulose composition maintained at a temperature below the temperature where gelation begins, withdrawing the pins and placing the pins in ovens at temperatures above the gelation temperature and drying the film. When the hot pins are dipped into the composition, the composition gels on the surface of the pin and as the pin is withdrawn, a film of gelled liquid of a certain thickness is formed on the pin. The pin is then generally turned 180° to an upright position and typically placed in the oven to dry. This technique is conventionally named "thermogelation". The dry capsule is then stripped, cut to size and the body and caps are fitted together. However, methyl cellulose is insoluble in water under 37° C.

U.S. Pat. No. 3,493,407, discloses the use of non-thermal gelling dip-molding compositions of some hydroxyalkylmethyl cellulose ethers in aqueous solvents. The pins must be kept in rotation for more than half an hour to obtain capsules with a regular shape.

U.S. Pat. No. 3,617,588, discloses the use of an induction heater to gel cellulose ether.

U.S. Pat. No. 4,001,211 discloses improved thermogelling compositions based on a blend of methyl cellulose and hydroxypropyl methyl cellulose.

The compositions and processes described above did not make it possible to obtain high-performance manufacturing of hard capsules both with regard to speed, dissolution properties and with regard to overall quality. Similarly, capsules manufactured by combination of HPMC with gelling agents have very poor visual quality and dissolution properties since they are sensitive to cations and to pH.

Research is still going on into compositions with even better qualities, particularly as regards the absence of defect, the visual aspect, high performance on filling machines, good dissolution properties and limited consumption of energy. Additives should be avoided as much as possible.

The FIGURE is a graph showing the gelling temperature of one embodiment of the disclosed hard capsules.

It is an object of the instant invention to provide new compositions particularly for the manufacture of HPMC capsules of high quality: e.g., standardized dimension, high transparency (similar to hard gelatine capsules), and excellent dissolution and mechanical performance.

This and other objects are achieved by a first aspect of the present invention which is an aqueous composition for the manufacture of hard capsules, wherein the composition comprises, in an aqueous solvent, 15-25% by weight, based on the total weight of the aqueous composition, of a hydroxypropyl methyl cellulose having a methoxy content of 27.0-30.0% (w/w), a hydroxypropoxy content of 4.0-7.5% (w/w) and a viscosity of 3.5-6.0 cPs as a 2% weight solution in water at 20° C.

In the present invention the HPMC methoxy and hydroxypropoxy contents are expressed according to the USP30-NF25.

In the present invention the viscosity of the HPMC 2% weight solution in water at 20° C. is measured according to the USP30-NF25 method for cellulose derivatives.

Preferably the aqueous composition comprises 17-23% by weight, based on the total weight of the aqueous composition, of the hydroxypropyl methyl cellulose.

Suitable hydroxypropyl methyl celluloses are commercially available. For example suitable types are all those fulfilling the requirements set forth in USP30-NF25 for HPMC type 2906.

Suitable aqueous compositions can be obtained by blending HPMCs of same type but different viscosity grade.

In a preferred embodiment, the HPMC in the aqueous composition of the invention is a HPMC having a viscosity of 4.0-5.0 cPs as a 2% w/w solution in water at 20° C.

Viscosity of the HPMC solution in water can be measured by conventional techniques, e.g., as disclosed in the USP by using a viscometer of the Ubbelohde type.

In an embodiment, the aqueous compositions of the invention may contain between 0% and 5%, preferably between 0% and 2% by weight based on the total weight of the aqueous composition of additional non animal-derived film-forming polymers typically used for the manufacture of hard capsules. Preferably, the HPMC aqueous compositions of the invention contain no other film-forming polymer beside the HPMC presently disclosed. Non animal-derived film-forming polymers are for example polyvinyl alcohol, plant-derived or bacterial-derived film-forming polymers.

Typical plant-derived film-forming polymers are starch, starch derivatives, cellulose, celluloses derivatives other than the HPMC as defined herein and mixtures thereof. Typical bacterial-derived film-forming polymer are exo-polysaccharides. Typical exo-polysaccharides are xanthan, acetan, gellan, welan, rhamsan, furcelleran, succinoglycan, scleroglycan, schizophyllan, tamarind gum, curdlan, pullulan, dextran and mixtures thereof.

In a preferred embodiment, the HPMC aqueous compositions of the invention contain between 0% and 1%, preferably 0% by weight based on the total weight of the aqueous composition of animal-derived materials conventionally used for the manufacture of hard capsules. A typical animal-derived material is gelatin.

In a preferred embodiment, the aqueous compositions of the invention contain less between 0% and 1%, preferably 0% by weight based on the total weight of the aqueous composition of a gelling system. By "gelling systems" it is meant one or more cations and/or one or more gelling agents. Typical cations are $K^+$, $Na^+$, $Li^+$, $NH_4^+$, $Ca^{++}$, $Mg^{++}$ and mixtures thereof. Typical gelling agent(s) are hydrocoloids such as alginates, agar gum, guar gum, locust bean gum (carob), carrageenans, tara gum, gum arabic, ghatti gum, khaya grandifolia gum, tragacanth gum, karaya gum, pectin, arabian (araban), xanthan, gellan gum, konjac mannan, galactomannan, funoran, and mixtures thereof. As usually, gelling agents can optionally be used in combination with cations and other ingredients such as sequestering agents.

As the HPMC aqueous compositions disclosed herein are suitable to give strong and physically stable gels without gelling systems, the dissolution properties of the HPMC capsules of the invention are not affected by the drawbacks typically associated with gelling systems, notably cations.

At the natural state—i.e. without the addition of pigments or similar ingredients in the composition—the HPMC hard capsules obtainable from the aqueous compositions of the invention show good clarity and transparency. The transmittance measured by UV at 650 nm on the capsule body (through its double shell layers) is around 80%, identical to gelatine hard capsules.

For obtaining coloured capsules at least one inert non-toxic pharmaceutical grade or food grade pigment such as titanium dioxide can be incorporated in the aqueous compositions. Generally, 0.001 to 1.0% by weight of pigment can be included in the aqueous composition. The weight is expressed over the total weight of the composition.

Optionally, an appropriate plasticizer such as glycerine or propylene glycol can be included in the aqueous solutions. To avoid an excessive softness, the plasticizer content has to be low, such as between 0% and 2%, more preferably between 0% and 1% by weight over the total weight of the composition.

The aqueous compositions of the invention can be prepared by dispersing the HPMC and the other optional ingredients in one or more aqueous solvents, preferably water. The aqueous solvent can be at a temperature above room temperature, preferably above 60° C., more preferably above 70° C. Optimal temperatures can be determined by the skilled person. In a preferred embodiment after de-bubbling, the dispersion is cooled down below room temperature, preferably below 15° C., to achieve the solubilisation of the HPMC.

The gelling temperature of the aqueous compositions may be determined by a measurement of the viscosity by progressively heating the composition. The temperature at which the viscosity starts to sharply increase is considered as the gelling temperature. As an example, for a concentration of about 19% w/w in water, any HPMC of the invention fulfilling the USP definition of HPMC type 2906 has a gelling temperature of about between 30 and 40° C. As an additional example, for concentrations between 15 and 25% w/w in water, an HPMC of the invention fulfilling the USP definition of HPMC with a hydroxypropoxy content of about 6%, has a gelling temperature between about 30 and 40° C. An example of how gelling temperature can easily be measured is provided in the examples.

The aqueous compositions of the invention can be used as dipping compositions in dip-molding processes for the manufacture of HPMC hard capsules.

It has been noted that the aqueous compositions of the invention allow the manufacture of good HPMC hard capsules showing optimal dissolution properties. Dissolution profile is a key point in therapy to obtain a complete and reproducible release of the substance contained in the capsule.

Additionally, it has been noted that the aqueous compositions of the invention allow the manufacture of good HPMC hard capsules whose bodies and caps, once telescopically joined, can suitably be sealed. This makes the presently disclosed new HPMC hard capsules a particularly good and cost-effective solution for the manufacture of liquid-filled oral dosage forms as well as powder-filled dosage forms for inhalation or the manufacture of tamper-proof pharmaceutical forms to be used in the context of double-blind trials.

In a second aspect, the present invention relates to a process for the manufacture of hydroxypropyl methyl cellulose hard capsules according to a dip coating process, characterized in that it comprises the steps of.

(a) providing an aqueous composition of a hydroxypropyl methyl cellulose having a methoxy content of 27.0-30.0% (w/w), a hydroxypropoxy content of 4.0-7.5% (w/w) and a viscosity of 3.5-6.0 cPs as a 2% weight solution in water at 20° C., wherein the concentration of the hydroxypropyl methyl cellulose in the aqueous composition is chosen to obtain a viscosity of the aqueous composition of 1000 to 3000 cPs, preferably 1200 to 2500 cPs, more preferably 1600 to 2000 cPs, measured at a temperature of 10° C. to 1.0° C. below the aqueous composition gelling temperature, (b) preheating dipping pins so that they are at 55-95° C. when dipped into the aqueous composition, (c) dipping the pre-heated dipping pins into the aqueous composition maintained at a temperature of 10° C. to 1.0° C. below its gelling temperature, (d) withdrawing the dipping pins from the aqueous composition obtaining a film on the dipping pins and (e) drying the film on the dipping pins at a temperature above the gelling temperature of the aqueous composition so as to obtain molded capsule shells on the pins.

Steps (a) and (b) can be performed in any order. By contrast, steps (c) to (e) are to be performed in the order they are presented and after steps (a) and (b).

In step (a) the aqueous compositions of the invention can be used. An optional adjustment of the HPMC concentration can be performed to meet the viscosity ranges indicated above.

In step (b), the temperature range of preheated pins is 55-95° C. meaning that this is the pin temperature when pins are dipped. Preferably the temperature is 60-90°, more preferably 60-85° C., more preferably 65-85° C., even more preferably 70-80° C. It is preferred that such temperature be chosen according to the desired capsule size. By "according to the capsule size" it is meant that the smaller the pin dimension, the higher the temperature. For example, for an HPMC type 2906 (USP classification) and within the HPMC weight ranges defined above for the aqueous composition, for a capsule size 00 (conventionally considered a large capsule size), the pin temperature is preferably between 70 and 80, for a capsule size 1 (conventionally considered a medium capsule size), the pin temperature is preferably between 80 and 90, and for a capsule size 4 (conventionally considered a small capsule size), the pin temperature is preferably between 85 and 95.

In step (c), the dipping composition is maintained at a temperature of 10° C. to 1.0° C., preferably 6° C. to 2.0° C., below its gelling temperature. For example, if a dipping composition has a gelling temperature of about 36.0° C., it can be maintained at a temperature of for example about 34.0° C.

After being withdrawn from the dipping composition, the pins can be turned from a "top-down" dipping position to a "top-up" drying position according to conventional capsule molding processes. In this step the pins are rotated about a horizontal axis of about 180° with respect to the dipping position of step (c).

By drying in step (e) the object is to reduce the water content in the capsule shells on the pins. Generally, the water content in the molded capsule shells is reduced from around 80% to around 7% by weight, based on the total weight of the molded capsule shells. An indicative water content in the capsule shell of the invention is provided below.

Step (e) can be performed according to any technique commonly known for this purpose, for example by placing the pins in conventional ovens, for a sufficient period of time, typically from 30 to 60 minutes.

In a preferred embodiment, step (e) is performed as disclosed in the co-pending patent application, filed by the instant Applicant on Oct. 26, 2006, having the title "Capsule formation" and having filing number U.S. 60/863,040. According to such a preferred embodiment, it has been found that subjecting the film to a particular combination of temperature and relative humidity provides excellent results.

Thus, preferably step (e) comprises a step (e1) where the dipping pins with the molded capsule shells are subjected to a temperature of 50 to 90° C. at a RH of 20 to 90%, preferably, T is 55 to 85° C. at a RH of 20 to 70%, more preferably T is 60 to 85° C. at a RH of 20 to 60%.

Generally the duration of step (e1) is 90-480 seconds, preferably 120-300 seconds, more preferably 120-240 seconds.

Step (e1) is preferably followed by a step (e2), where the pins are subjected to a temperature of 30 to 60° C. at a RH of 20 to 90%, preferably, T is 35 to 55° C. at a RH of 20 to 70%, more preferably T is 35 to 50° C. at a RH of 20 to 60%.

Generally the duration of step (e2) is 30 to 60 minutes.

Both steps (e1) and (e2) can be performed in an oven. The ovens used are preferably tunnels which allow a continuous processing.

The term "relative humidity" is used herein to mean the ratio of the actual water vapor pressure at a given temperature to the vapor pressure that would occur if the air were saturated at the same temperature. There are many technologies for humidity measurement instruments known to the skilled person, all of which would give substantially the same RH measure.

In the current description, if not otherwise indicated, by "capsule" it is meant a hard capsule consisting of two co-axial, telescopically-joined parts, referred to as body and cap. Normally, caps and bodies have a side wall, an open end and a closed end. The length of the side wall of each of said parts is generally greater than the capsule diameter. Thus, the HPMC hard capsules of the present invention do not structurally depart from the conventional definition of hard capsules. "Capsule" refers to both empty and filed capsules.

The molded capsule shells mentioned to above, generally refer to both bodies and caps, depending on the shape of the mold pin. Thus, after step (e) the dried capsule shells on the dipping pins can be processed according to conventional steps. This means that in general after step (e), the capsule shells (bodies and caps) are stripped from the pins. This step can be followed by cutting the stripped shells to a desired length.

Typically, hard capsule dip-molding manufacturing processes encompass an additional step of lubricating the pins so as to make it easier to strip the capsule shells from the pins. Lubrication is normally achieved via the application of a demolding agent to the pins surface.

In the instant invention any demolding agent and lubricating apparatus conventionally used for HPMC capsules can be used.

After stripping and cutting, the bodies and caps may be fitted together for obtaining a complete capsule. Preferably, the capsule cap and body are telescopically joined together so as to make their side walls partially overlap and obtain a capsule.

"Partially overlap" also encompasses an embodiment wherein the side walls of caps and bodies have substantially the same length so that, when a cap and a body are telescopically joined, the side wall of said cap encases the entire side wall of said body. This embodiment is particularly advantageous for the manufacture of tamper-proof capsules to be used for example in the context of double-blind trials.

In one embodiment, the dipping pins are designed so as to create pre-locking means in caps and bodies formed thereon. Suitable pins design and pre-locking means are disclosed for example in EP 110500 B1, notably lines 27-31 of column 2 and for example FIG. 34. If caps and bodies are provided with pre-locking means, the bodies and caps obtained after stripping, are first jointed to obtain a pre-locked capsule. This pre-locked capsule can then be re-opened, filled and locked to its final position.

Once filled, the capsules can be made tamper-proof by using any solution conventionally used in the field of hard capsules to make the joint permanent. Banding or sealing are suitable techniques. Sealing is a technique well known in the field of hard shell capsules. Various alternative techniques are currently used for this purpose. A suitable procedure is disclosed for example in U.S. Pat. Nos. 4,539,060 and 4,656,066. Many improvements of sealing procedure are currently available.

According to a know sealing process, the capsule is (i) contacted with a sealing fluid, (ii) excess sealing fluid is removed from the surface and (iii) the capsule is dried so as to induce curing and make the seal permanent.

For the HPMC capsules obtained with the invention, alcohol/water mixtures can be used as sealing fluids, such as ethanol/water mixtures.

The good sealing quality obtained makes the sealed capsule of the instant invention particularly suitable for the manufacture of leakage-free dosage forms particularly for use in the administration of substances in liquid form. By "sealing quality" it is meant either the visual quality and/or the adhesion strength of the sealing.

The above aqueous compositions and process are particularly suitable for manufacturing HPMC hard capsules that dissolve at a rate comparable to conventional gelatine capsules. Such capsules can be manufactured at an industrial scale with process speeds comparable to gelatine capsules. Their mechanical properties are better than those of conventional gelatine capsules since they are less brittle, particularly under extremely dry atmosphere. Their visual appearance is similar to that of gelatine capsules.

In a third aspect, the present invention relates to a HPMC hard capsule shell containing a HPMC having a methoxy content of 27.0-30.0% (w/w), a hydroxypropoxy content of 4.0-7.5% (w/w) and a viscosity of 3.5-6.0 cPs as a 2% weight solution in water at 20° C., wherein the methoxy and hydroxypropoxy contents are expressed according to the USP30-NF25 and wherein the viscosity is measured according to the USP method for cellulose derivatives.

In a preferred embodiment, the capsule shells are obtainable by the aqueous composition and/or process disclosed above.

In a preferred embodiment, the capsule shell contains the HPMC in an amount between 70 and 99%, preferably between 80 and 99% by weight based on the shell weight. If no other film-forming polymers are present, the HPMC is preferably between 92% and 99%, more preferably between 93 and 98%, even more preferably between 94% and 97% by weight based on the shell weight.

In a preferred embodiment, the capsule shell contains between 0% and 25%, preferably between 0% and 10% by weight based on the shell weight of additional non animal-derived film-forming polymers as defined above.

In a preferred embodiment, the capsule shell contains water between 1 to 8%, preferably between 7 and 2%, more preferably between 6 and 3% by weight based on the shell weight.

In a preferred embodiment, the capsule shell contains one or more pigments as those discussed above, between 0 and 10%, preferably between 0.001 and 5%, more preferably between 0.01 and 3%, by weight based on the shell weight.

In a preferred embodiment, the capsule shell contains one or more dyes between 0 and 5%, preferably between 0.001 and 3%, more preferably between 0.01 and 2%, by weight based on the shell weight.

In a preferred embodiment, the capsule shell contains one or more plasticizers as those discussed above, between 0 and 10%, preferably between 0.001 and 5%, more preferably between 0.01 and 3%, by weight based on the shell weight.

In a preferred embodiment, the capsule shell contains one or more antibacterial agents between 0 and 2%, preferably between 0.001 and 1%, more preferably between 0.01 and 0.5%, by weight based on the shell weight.

In a preferred embodiment, the capsule shell contains one or more flavourings agents between 0 and 2%, preferably between 0.001 and 1%, more preferably between 0.01 and 0.5%, by weight based on the shell weight.

In a preferred embodiment, the HPMC hard capsule shell presently disclosed can be used for the manufacture of tamper-proof pharmaceutical dosage forms. To this end, it is particularly advantageous if the capsule shell is as disclosed in EP 110500 B1. In this preferred embodiment, the HPMC hard capsule shell comprises coaxial cap and body each of the cap and body having a generally cylindrical side wall, an open end and a closed end region, the side wall of each of said parts is substantially greater than the capsule shell diameter, the cap and body being adapted to be joined in telescopic relationship wherein, when the cap and body are fully joined in telescopic relationship, the only portion of the body which is exposed is the closed end region, and wherein the closed end region has an outer surface which is of such a configuration as to resist being gripped, whereby separation of the cap and body is impeded, and wherein when the cap and body are fully joined in telescopic relationship, the inner side wall of the cap is substantially totally overlapped by the outer side wall of the body. In other words, when the cap and body are fully joined in telescopic relationship, the side wall of the cap encases the entire side wall of the body. Thus, in use, only the body dosed end is exposed and presents a minimal surface for gripping and withdrawal of the body from within the cap, thereby impeding separation of the capsule shell.

The closed end region of either the body and the cap may, for example, have a configuration which is generally hemispheroidal, pyramidal, conical or flat.

For additional security, it is preferred that the body and the cap further include mutual locking means comprising one or more circumferentially extending ridges and/or grooves. Thus, the capsule shell may be such that the side wall of one of the cap and body has a locking means comprising one or more circumferentially extending ridge extending either (i) radially inwardly from an inner surface of the side wall of the cap or (i) radially outwardly from an outer surface of the side wall of the body, as the case may be.

Alternatively, or in addition, the side wall of the other of the cap and body has one or more circumferentially extending groove extending either (i) radially inwardly from the outer surface of the body or (ii) radially outwardly from the inner surface of the cap, as the case may be, and engaging a respective ridge.

It is preferred that the capsule shell further includes venting means to permit air to escape from within the capsule when joined, wherein the or each circumferentially extending ridge comprises two or more segments so that spaces between the segments act as vents to permit air to escape from within the capsule when the cap and body are being joined.

It is preferred that the side wall of one of the cap and body has a pair of diametrically opposed integral indents extending either (i) radially inwardly from the inner surface of the side wall of the cap or (ii) radially outwardly from the outer surface of the side wall of the body, as the case may be; and the diametric spacing of the indents is, in the case (i), less than the outside diameter of the open end of the body or, in the case (ii), greater than the inside diameter of the open end of the cap, such that the body can enter the cap and permit air to escape from within the capsule when the cap and body are being joined.

For storage and/or transportation purposes, it is preferred that the capsule shell may also include means for pre-locking the partially joined caps and bodies in a constant predetermined relative position prior to filing and final joining. This embodiment is particularly advantageous when it is desired to include step [I-1] in the process of the invention.

Preferably, bodies have a reduced diameter in the area of their open end in order to avoid abutment when they are telescopically housed within caps.

Alternatively, or in addition, caps have a reduced diameter in the area of their open end, thereby resulting in improved engagement between them and the region of the side wall of the bodies adjacent the dosed end region of the bodies, as further resistance to tampering.

In a fourth aspect the present invention relates to a HPMC hard capsule comprising a capsule shell as defined above and one or more substances filled therein.

All kinds of suitable compounds may be filed in the capsule of the present invention including pharmaceuticals, vitamins or nutrients, plant powder extracts etc, including particularly hygroscopic ingredients.

When used as dosage form for drugs, capsules of the invention typically comprise for example from 0.001 g to 2.0 g of active ingredient, optionally mixed with one or more pharmaceutically acceptable excipients.

In one embodiment, the HPMC hard capsule presently disclosed, optionally sealed, can be used in the context of dry powder inhalers (also commonly know by the acronym DPIs). In this embodiment, the superiority of the presently disclosed capsules over conventional HPMC capsules can be traced back for example to:
- capsules improved colour/transparency,
- reduced stickiness of the internal surface of caps and bodies side walls due for example to a reduced amount of demolding agent required in capsule manufacturing process,
- improved quality of capsule sealing.

All of the capsule embodiments disclosed above can be produced on conventional capsule-making machines utilizing dip-moulding technology. The skilled person can find additional background information on dip-moulding process for gelatine capsules in U.S. Pat. No. 4,893,721.

In a fifth aspect, the present invention relates to hydroxypropyl methyl cellulose hard capsule shells and capsules as defined above, for use in the administration to a subject of substances, particularly pharmaceutical substances, in liquid or solid form.

In a sixth aspect, the present invention relates to the use of hydroxypropyl methyl cellulose hard capsule shells and capsules as defined above for the manufacture of pharmaceutical dosage forms suitable for the administration to a subject of pharmaceutical substances in liquid or solid form.

By "solid form" it is preferably meant powder form, and the administration of the substance(s) may preferably entail the use of a dry powder inhaler.

By "subject" it is preferably meant a human or animal subject, more preferably a human subject.

Preferred conditions for implementing the compositions described above also apply to the other subjects of the invention envisaged above such as processes and capsules.

The scope of the invention can be understood better by referring to the examples given below, the aim of which is to explain the advantages of the invention. Unless otherwise specified, all parts and percentages are by weight. Composition viscosities were determined by Brookfield viscometer.

EXAMPLE 1

Aqueous Composition for the Manufacture of Hydroxypropyl Methyl Cellulose Hard Capsules A 5 kg composition of 18.8% HPMC type 2906 (methoxy content 28.7%, hydroxypropoxy content 5.4%) of 4.4 cPs viscosity at 2% concentration (w/w) was prepared as follows:

The HPMC powder is dispersed into hot water at 75° C. under stirring. Formation of foam is observed. After complete dispersion of the powder, the temperature is kept at 75° C. under very gentle stirring for de-foaming of the dispersion. Then the dispersion is cooled down to 10° C. under gentle stirring for obtaining dissolution of the HPMC. After keeping the composition for more than 30 minutes at 10° C., a dipping composition ready for use in capsule manufacturing is obtained.

The HPMC composition gelling temperature was determined by viscosity measurement by progressively heating the composition. The gelling temperature found was 34° C.

EXAMPLE 2

Manufacture of Hard Capsules

The composition prepared in example 1 is poured into the dipping dish of a pilot equipment of hard capsule manufacturing. The dip pins of size 0 are pre-heated at 75° C., while the dipping composition is maintained at 32° C. At this temperature, the viscosity of the dipping composition was 2000 cPs. Capsules of size 0 are manufactured by the conventional dipping process, but with the pre-heated pins. After the dipping, the capsules are dried in an oven with hot air at 60° C. and 40% RH for 3 minutes then with hot air at 40° C. and 40% RH.

The capsules obtained are of high quality: good and standardized dimension (the top wall thickness is >140 µm), high transparency (similar to hard gelatin capsules), excellent dissolution and mechanical performance.

EXAMPLE 3

Optimal Pre-Heating Temperature for Pins

Example 2 was re-run but with dip pins pre-heated at 60° C. instead of 75° C. It is noted that pin size 0 is considered a medium-large dimension.

The gelling on the pins after dipping was not optimal to obtain commercially acceptable capsules. Solution partially flew down the pin during drying, leading to the top wall thickness less than 50 µm.

Conclusion: 60° C. as pin pre-heating temperature is less preferable than 75° C. for size 0 capsule manufacturing.

EXAMPLE 4

Mechanical Properties Under Stress Conditions of the Capsules of Example 2

The mechanical properties of the capsules of example 2 were tested under stress conditions as follows: A stainless steel cylinder weighing 100 g was allowed to fall from a height of 8 cm onto empty capsules one by one. The percentage of broken capsules is reported hereunder.

Results:

| | % of broken capsules | |
|---|---|---|
| Storage conditions RH % | Capsules of example 2 | Gelatine capsules |
| 2.5 | 0 | 24 |
| 10 | 0 | 13 |
| 23 | 0 | 2 |
| 33 | 0 | 0 |
| 50 | 0 | 0 |

RH = Relative Humidity

Conclusions: capsules of example 2 do not exhibit any brittleness even at extremely low relative humidity.

EXAMPLE 5

In Vitro Dissolution Performance of the Capsules of Example 2

The capsules of example 2 were tested according to the USP monograph method for dissolution of acetaminophen capsules.
Results:

| Dissolution medium | Time | % Acetaminophen dissolved |
|---|---|---|
| pH 1.2 | 15 min | 32 |
| | 30 min | 68 |
| | 45 min | 88 |
| | 60 min | 95 |
| | 75 min | 100 |
| Demineralised water | 15 min | 36 |
| | 30 min | 70 |
| | 45 min | 88 |
| | 60 min | 95 |
| | 75 min | 98 |
| pH 6.8 potassium phosphate | 15 min | 29 |
| | 30 min | 67 |
| | 45 min | 87 |
| | 60 min | 96 |
| | 75 min | 99 |

EXAMPLE 6

Determination of the Gelling Temperature

A 18.8% w/w solution in water of HPMC type 2906 is prepared as described in example 1. The viscosity is monitored with a Brookfield Model DV-II viscometer at different temperatures by increasing the measure cell temperature by steps (with 10 minutes equilibrium at each step). The results are shown in the FIGURE. It can immediately be appreciated that the gelling temperature is around 34° C.

COMPARATIVE EXAMPLE 1

Manufacture of Capsules with HPMC Type 2910

A 5 kg composition of 26.3% HPMC type 2910 of 3 cPs viscosity at 2% was prepared as in examples 1 and 2. The gelling temperature found was 47° C. While the dipping composition is maintained at 45° C.

Capsules of size 0 were manufactured under the same process conditions as in the above example 2 (viscosity of the dipping composition 2000 cPs at 45° C.).

Results: an acceptable dimension is obtained (the top wall thickness is above 140 μm). However, too brittle capsules are obtained since almost al the capsules break during their stripping from the dipping pins.

COMPARATIVE EXAMPLE 2

Manufacture of Capsules with HPMC Type 2910

A 5 kg composition of 17.9% HPMC type 2910 of 6 cPs viscosity at 2% was prepared as in examples 1 and 2. The gelling temperature found was 50° C. While the dipping composition is maintained at 48° C. Capsules of size 0 were manufactured under the same process conditions as in the above example 2 (viscosity of the dipping composition 2000 cPs at 48° C.).

Results: an unacceptable dimension is obtained (insufficient gelling behaviour, composition on the pins partly flowing down, top wall thickness less than 80 μm). Therefore, the advantage in using an HPMC type 2906 against using other HPMCs such as HPMC type 2910 can be seen.

COMPARATIVE EXAMPLE 3

Manufacture of Capsules with Too Low Dipping Solution Viscosity

Example 2 was re-run but with a dipping solution of a viscosity at 900 cPs measured at 32° C. This decrease in viscosity was obtained by adding water to the composition.

The gelling on the pins after dipping was not sufficient, solution flowing down occurred during the drying, leading to the top wall thickness less than 50 μm, much too low for being acceptable. Results: a viscosity of 900 cPs for the dipping solution is too low to have an acceptable gelling ability and top wall thickness.

The invention claimed is:
1. A process comprising:
   forming hydroxypropyl methyl cellulose hard capsules using thermogelation by:
   (a) providing an aqueous composition of a 2906 hydroxypropyl methyl cellulose having a methoxy content of 27.0-30.0% (w/w), a hydroxypropoxy content of 4.0-7.5% (w/w) and a viscosity of 3.5-6.0 cPs as a 2% weight solution in water at 20° C., wherein the aqueous composition is substantially free of gelling agent;
   (b) dipping heated dipping pins into the aqueous composition, wherein the aqueous composition is maintained at a temperature below a gelling temperature of the aqueous composition,
   (c) withdrawing the dipping pins from the aqueous composition obtaining a film on the dipping pins; and
   (d) drying the film on the dipping pins so as to obtain molded capsules on the pins.
2. The process of claim 1 wherein the hydroxypropyl methyl cellulose is present in a range from 15 to 25% by weight, based on the total weight of the aqueous composition.
3. The process of claim 1 wherein the dipping pins are heated such that the dipping pins are 55-95° C. when dipped into the aqueous composition.
4. The process of claim 1 wherein the dipping pins are heated such that the dipping pins are 60-90° C. when dipped into the aqueous composition.
5. The process of claim 1 wherein the aqueous composition in step (b) is maintained at a temperature of 10° C. to 1.0° C. below a gelling temperature of the aqueous composition.
6. The process of claim 1 wherein step (d) comprises (d1) exposing the pins to an environment having temperature of 50-90° C. and a relative humidity of 20-90%.
7. The process of claim 6 wherein the temperature is 60-85° C. and the relative humidity is 20-60%.
8. The process of claim 6 wherein after (d1) the pins are exposed to a temperature of 30-60° C. and a relative humidity of 20-90% as step (d2).
9. The process of claim 8 wherein the duration of step (d2) is between 30 and 60 minutes.
10. A hard capsule formed by the process of claim 1.

11. A hydroxypropyl methyl cellulose hard capsule shell comprising:
   a thermogelled hard capsule shell comprising hydroxypropyl methyl cellulose 2906 having a methoxy content of 27.0-30.0% (w/w), a hydroxypropoxy content of 4.0-7.5% (w/w) and a viscosity of 3.5-6.0 cPs as a 2% weight solution in water at 20° C., wherein the 2908 hydroxypropyl methyl cellulose is present in an amount ranging from 70% to 99% by weight of the shell weight.

12. The capsule shell of claim 11 wherein the hydroxypropoxy methyl cellulose is present in an amount between 70% and 90% by weight on the shell weight.

* * * * *

UNITED STATES PATENT AND TRADEMARK OFFICE
CERTIFICATE OF CORRECTION

PATENT NO. : 9,655,860 B2
APPLICATION NO. : 15/378856
DATED : May 23, 2017
INVENTOR(S) : Cade et al.

It is certified that error appears in the above-identified patent and that said Letters Patent is hereby corrected as shown below:

In the Claims

Column 13 In Claim 11, Line 7, "2908" should be --2906--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*